US005985668A

United States Patent [19]
Mattes et al.

[11] Patent Number: 5,985,668
[45] Date of Patent: Nov. 16, 1999

[54] SUCROSE METABOLISM MUTANTS

[75] Inventors: Ralf Mattes; Kathrin Klein; Sabine Stegmaier, all of Stuttgart, Germany

[73] Assignee: Südzucker Aktiengesellschaft Mannheim/Ochsenfurt, Mannheim, Germany

[21] Appl. No.: 08/673,190

[22] Filed: Jun. 27, 1996

[30] Foreign Application Priority Data

Jun. 28, 1995 [DE] Germany .......................... 195 23 560

[51] Int. Cl.$^6$ .......................... C12N 15/70; C12N 15/00; C12N 1/21; C12N 15/63
[52] U.S. Cl. .......................... 435/471; 435/91.1; 435/94; 435/100; 435/183; 435/233; 435/252.3; 435/252.33; 435/252.34; 435/320.1; 435/440; 435/463; 536/23.1; 536/23.2; 536/23.7
[58] Field of Search ................................. 435/243, 252.3, 435/183, 233, 94, 471, 252.33, 100, 463, 91.1, 440, 320.1, 252.34; 536/23.1, 23.2, 23.7

[56] References Cited

U.S. PATENT DOCUMENTS

| | | | |
|---|---|---|---|
| 4,359,531 | 11/1982 | Bucke et al. | 435/97 |
| 4,390,627 | 6/1983 | Lantero, Jr. | 435/180 |
| 4,670,387 | 6/1987 | Bucke et al. | 435/97 |
| 4,788,145 | 11/1988 | Munir | 435/100 |
| 4,857,461 | 8/1989 | Egerer et al. | 435/94 |
| 5,229,276 | 7/1993 | Sugitani et al. | 435/97 |
| 5,336,617 | 8/1994 | Sugitani et al. | 435/252.1 |

OTHER PUBLICATIONS

Jahreis, et al. 1993, Molecular Microbiology, vol. 9 No. 1 pp. 195–209.

Sprenger, et. al. 1988. J. General Microbiology, vol. 134, pp. 1635–1644.

Hartmeier, W. "Immobilized Biocatalystsi An Introduction", 1986, Springer–Verlag, (English Translation), see esp. pp. 139–144.

Bockmann, J. et al, 1992. Mol. Gen. Genet. vol. 235, pp. 22–32.

Joklik et al., "Zinsger Microbiol.: 18th Ed." 1984, Escecially Ch 35.

Venetia A. Saunders et al., "Microbial Genetics Applied to Biotechnology", Croom Helm Ltd., Provident House, Burrell Row, Beckenham, kent BR 3 1AT, 1987, pp. 206–211.

E. Wagner, et al., "Cloning and characterization of the scrA gene encoding the sucrose–specific Enzyme II of the phosphotransferase system from *Staphylococcus xylosus*", Mol. Gen. Genet., Oct. 1993, 241(1–2):33–41.

YY Chen et al., "Sequence analysis of scrA and acrB from *Streptococcus sobrinus* 6715", Infect. Immun., Jun. 1993; 61(6): 2602–2610.

Tsuyuki K. et al. "Isolation and Characterization of Isomaltulose–and Trehalulose–Producing Bacteria From Thailand Soil," (Jul. 2, 1992), vol. 38, pp. 483–490.

Cheetham, P.S.J. et al. "The formation of isomaltulose by immobilized *Erwinia rhapontici*" Nature (Oct. 14, 1982), vol. 299, pp. 628–631.

Miyata, Y. et al. "Isolation and characterization of *Pseudomonas mesoacidophila* producing trehalulose" *Bioscience, Biotechnology, and Biochemistry* (Oct. 1992), vol. 56, No. 10, pp. 1680–1681.

Nagai, Y. et al., "Characterization of α–Glucosyltransferase from *Pseudomonas Mesoacidophila* MX–45" Biosci. Biotech. Biochem, 58(10):1789–1793, 1994.

Bugaenko, I.F., "Sweetening substances on the basis of sucrose," *Chemical Abstracts*, 1993–1994.

Ioroi, R., et al., "Oligosaccharide Production by Dextransucrase of Streptococcus bovis No. 148 Isolated from Bovine Rumen," *Nippon Shokuhin Kogyo Gakkaishi*, vol. 37, 5:355–362 (1990).

Itoh, Y., et al., "Synthesis of Leucrose by Dextransucrase and Some Conditions for the Reaction," *Nippon Shokuhin Kogyo Gakkaishi*, vol. 37, 3:171–177 (1990).

Iizuka, M., et al., "Susceptibility of leucrose to carbohydrases," *Biological Abstracts*, Jun., 1991.

Crabb, W.D., et al., "Tools and Strategies for Cloning Studies," in Streips and Yasbin *Modern Microbial Genetics*, pp. 365–388, 1991.

Brock, T.D., et al., "Kinds of Plasmids and Their Biological Significance," *Biology of Micro–Organisms*,Prentice–Hall, Inc., Chapter 8, Section 7.6–7.9, pp. 278–314, 1988.

Cheetam, P.S.J. (1984) "The extraction and mechanism of a novel isomaltulose–synthesizing enzyme from *Erwini rhapontici,"Biochem. J.*, 220:213–220.

Ernst–L. Winnacker, "From Genes to Clones: Introduction to Gene Technology" (1987), pp. 383–395.

Bockmann, J., et al., "Characterization of a chomosomaly encoded, non–PTS metabolid pathway for sucrose utiliztion in *Escherichia coli* EC3132," Mol Gen Genet, 235:22–32 (1992).

Joklik, W. et al., "Enterobacteriaceae: General Characteristics," *Zinsser Microbiology*, 18th Ed., pp. 595–601 (1968).

Hartmeier, W., "Immobilized Biocatalysts: An Introduction," *Springer–Verlag*, pp. 139–144 (1986).

Jahreis, K. and Lengeler, J., "Molecular analysis of two ScrR repressors and of a ScrR–FruR hybrid repressor for sucrose and D–frutose specific regulons from enteric bacteria," *Molecular Microbiology*, 9(1):195–209 (1993).

Sprenger, G. and Lengeler, J., "Analysis of Sucrose Catabolism in *Klebsiella penumoniae* an in Scr+ Derivatives of *Escherichia coli* K 12," J. Gen. Microbiology, 134:1635–1644 (1988).

Primary Examiner—John L. LaGuyader
Assistant Examiner—Mark L. Shibuya
Attorney, Agent, or Firm—Finnegan, Henderson, Farabow, Garrett & Dunner, L.L.P.

[57] ABSTRACT

The invention relates to sucrose isomerases, to DNA sequences coding therefor, and to novel processes for producing noncariogenic sugars.

30 Claims, 6 Drawing Sheets

SUCROSE METABOLISM MUTANTS

DESCRIPTION

The present invention relates to an improved process for preparing noncariogenic sugars, in particular trehalulose or/and palatinose, using recombinant DNA technology.

The acariogenic sugar substitutes palatinose (isomaltulose) and trehalulose are prepared industrially from sucrose by an enzymatic rearrangement using immobilized bacterial cells (for example of the species *Protaminobacter rubrum, Erwinia rhapontici, Serratia plymuthica*). This entails the α1→β2 glycosidic linkage existing between the two monosaccharide units in the disaccharide sucrose being isomerized to an α1→6 linkage in the case of palatinose and to an α1→α1 linkage in the case of trehalulose. This sucrose re-arrangement to the two acariogenic disaccharides takes place with catalysis by the bacterial enzyme sucrose isomerase, also called sucrose mutase. This reaction results in a product mixture which, depending on the organism used, comprises in addition to the required acariogenic disaccharides palatinose and trehalulose also certain contents of unwanted monosaccharides (glucose or/and fructose). These monosaccharide contents are a considerable industrial problem because elaborate purification procedures (usually fractional crystallizations) are necessary to remove them.

In the production of acariogenic disaccharides it is possible for monosaccharides to be produced on the one hand by degradation of the required final products palatinose or/and trehalulose and on the other hand by degradation of the sucrose starting material. PCT/EP95/00165 (corresponding to U.S. Pat. No. 5,786,140) proposes cells which display a reduced palatinose or/and trehalulose metabolism, that is to say are able to utilize these disaccharides metabolically to only a small extent. Cells which display a diminished sucrose metabolism are not disclosed in PCT/EP95/00165.

One object on which the present invention was based was thus to suppress as far as possible the degradation of sucrose to monosaccharides in the preparation of trehalulose or/and palatinose. Another object on which the present invention was based was to provide organisms which produce palatinose or/and trehalulose in higher yield than known organisms.

To achieve these objects, cells deficient in sucrose metabolism, a process for their preparation and an improved process for preparing noncariogenic sugars, especially palatinose or/and trehalulose, are provided.

The invention relates on the one hand to a cell which comprises at least one DNA sequence coding for a protein with a sucrose isomerase activity and displays a reduced sucrose metabolism.

In connection with the present invention, the term "protein with a sucrose isomerase activity" is intended to embrace those proteins capable of isomerizing sucrose to other disaccharides, with the α1→β2 glycosidic linkage between glucose and fructose in the sucrose being converted into another glycosidic linkage between two monosaccharide units, especially into an α1→6 linkage or/and an α1→α1 linkage. The term "protein with a sucrose isomerase activity" therefore particularly preferably relates to a protein able to isomerize sucrose to palatinose or/and trehalulose. Moreover the content of palatinose and trehalulose in the total disaccharides formed by isomerization of sucrose is preferably ≧2%, particularly preferably ≧20% and most preferably ≧50%.

Examples of cells which comprise nucleotide sequences coding for a protein with sucrose isomerase activity are, in particular, microorganisms of the genera Protaminobacter, Erwinia, Serratia, Leuconostoc, Pseudomonas, Agrobacterium, Klebsiella and Enterobacter. Specific examples of such microorganisms are *Protaminobacter rubrum* (CBS 547,77), *Erwinia rhapontici* (NCPPB 1578), *Serratia plymuthica* (ATCC 15928), *Serratia marcescens* (NCIB 8285), *Leuconostoc mesenteroides* NIRL B-521f (ATCC 10830a), *Pseudomonas mesoacidophila* MX-45 (FERM 11808 or FERM BP 3619), *Agrobacterium radiobacter* MX-232 (FERM 12397 or FERM BP 3620), Klebsiella subspecies, and Enterobacter species.

Specific examples of proteins with sucrose isomerase activity and nucleic acids coding therefor from *P. rubrum, E. rhapontici*, Enterobacter spec. SZ 62 and *P. mesoacidophila* are described in U.S. Pat. No. 5,786,140. The disclosure in this patent application is incorporated herein by reference.

The term "reduced sucrose metabolism" means for the purpose of the present invention that a cell is able to utilize sucrose metabolically by degradation to monosaccharides to a smaller extent than a corresponding wild-type cell. This means that in the cells according to the invention at least one metabolic pathway which brings about degradation of sucrose to unwanted by-products, especially glucose or fructose, is partly or completely blocked. Hence the metabolic utilization of sucrose in the cells according to the invention takes place to a greater extent by isomerization of sucrose to acariogenic disaccharides, especially palatinose and trehalulose. A cell according to the invention is therefore able to produce higher contents of the noncariogenic disaccharides trehalulose or/and palatinose and diminished amounts of the interfering by-products glucose and fructose than a wild-type cell. The reduction in sucrose metabolism can take place, for example, by partial or complete inhibition of the expression of at least one gene which codes for a sucrose metabolizing enzyme. If the wild-type cell which is used as starting material for preparing sucrose metabolism mutants has more than one metabolic pathway for utilizing sucrose, it is preferred to inhibit or to block all the metabolic pathways where possible.

The present application describes the isolation of gene sections which code for enzymes of sucrose metabolism from *P. rubrum* and Enterobacter spec. SZ 62. Moreover partial sequences of these gene sections which are partly homologous with known genes for sucrose metabolism from Salmonella or Klebsiella have been determined. These isolated gene sections thus confer on transformed *E. coli* cells the ability to metabolize sucrose.

To produce cells according to the invention with diminished sucrose metabolism, parts are deleted from the isolated gene sections by digestion with restriction endonucleases. It is possible in this way to identify DNA sequences whose complete or partial deletion leads to inactivation of sucrose metabolism in *E. coli*. These deletions can be backcrossed, for example by appropriate known methods, into other microorganisms and established in the chromosome by homologous recombination. This results in deletion mutants, according to the invention, of the initial strains which have permanently lost the ability to metabolize sucrose. Examples of such deletion mutants of *Protaminobacter rubrum* and Enterobacter SZ 62 are described.

On investigation of the deletion mutants prepared according to the invention it was found that considerably lower monosaccharide concentrations are obtained by comparison with the wild type with intact sucrose metabolism. This result is achieved both in mixtures in the test tube and with immobilized cells on the laboratory scale.

It has furthermore been found, surprisingly, that a sucrose deletion mutant of *Protaminobacter rubrum* is capable of constitutive expression of sucrose isomerase. It is therefore in fact possible to produce acariogenic sugars without adding sucrose to the medium.

A number of genes from *Protaminobacter rubrum* and Enterobacter species SZ 62 which code for sucrose metabolizing enzymes have been identified. These genes are located on the plasmids pKAT 101, pKAT 102, pKAT 103 and pSST 3001. These plasmids have been deposited at the Deutsche Sammlung von Mikroorganismen und Zellkulturen GmbH (DSM), Mascheroder Weg 1b, D-38124 Braunschweig under deposit numbers 10030 (pKAT 101), 10031 (pKAT 102), 10032 (pKAT 103) and 10033 (pSST 3001) in accordance with the provisions of the Budapest Treaty.

Hence a first embodiment of the present invention relates to a cell in which the reduction of sucrose metabolism takes place by partial or complete inhibition of the expression of DNA sequences on the plasmids pKAT 101 (DSM 10030) and pKAT 103 (DSM 10032) or DNA sequences homologous therewith. The homology with the sequences on pKAT 101 and pKAT 103 is preferably at least 70%, particularly preferably at least 80% and most preferably at least 90% at the nucleotide level. The DNA sequences on pKAT 101 and pKAT 103 were isolated from *P. rubrum* and code for enzymes involved in the metabolism of sucrose. It is possible by deleting one or more gene sections to cause the *P. rubrum* cell to lose its ability to utilize sucrose via the relevant metabolic pathway. Part-sections of the DNA sequences from pKAT 101 are shown in the appended sequence listings SEQ ID NO. 1–3. These sequences are, at the level of the translated regions, 68–83% homologous with sections of the genes for scrR, scrB and scrA of the bacterium *Klebsiella pneumoniae* (Jahreis and Lengeler, Mol. Microbiol. 9 (1993), 195–209). FIGS. 1 and 2 depict the plasmid maps of pKAT 101 and pKAT 103, indicating the sequenced part-sections. FIG. 3a shows a comparison of the sequenced sections with the regions homologous therewith from *K. pneumoniae*.

Besides the nucleotide sequences depicted in the sequence listings, the present invention also embraces DNA sequences which hybridize with one of these sequences. The term "hybridization" according to the present invention is used as in Sambrook et al. (Molecular Cloning. A Laboratory Manual, Cold Spring Harbor Laboratory Press (1989), 1.101–1.104). According to the present invention, hybridization is the word used when a positive hybridization signal is still observed after washing for 1 hour with 1×SSC and 0.1% SDS at 55° C., preferably at 62° C. and particularly preferably at 68° C., in particular for 1 hour in 0.2×SSC and 0.1% SDS at 55° C., preferably at 62° C. and particularly preferably at 68° C. A nucleotide sequence which hybridizes under such washing conditions with one of the nucleotide sequences indicated in the sequence listings is a nucleotide sequence according to the invention.

A second embodiment of the present invention relates to a cell in which the reduction in sucrose metabolism takes place by partial or complete inhibition of the expression of DNA sequences on the plasmid pSST 3001 (DSM 10033) or sequences homologous therewith. The DNA sequences on pSST 3001 were isolated from Enterobacter spec. SZ62 and code for enzymes involved in the metabolism of sucrose. Deletion of one or more gene sections can cause the Enterobacter cell to lose its ability to utilize sucrose via the relevant metabolic pathway. The DNA sequences are preferably selected from the nucleotide sequences shown in the sequence listings SEQ ID NO. 4–9 or nucleotide sequences hybridizing therewith. The sequences found have a high degree of homology with regions in the scr operon of *K. pneumoniae* (Jahreis and Lengeler, supra). The sequenced partial regions are, at the level of the translated sequence, 93–99% homologous with the sections for scrK, scrY, scrB, scrA and scrR from *K. pneumoniae*. FIG. 4 shows the plasmid map of pSST 3001, indicating the sequenced part-sections. FIG. 3b shows a comparison of these sections with the regions homologous therewith from *K. pneumoniae*.

In a third embodiment of the present invention, the reduction in sucrose metabolism takes place by partial or complete inhibition of the expression of DNA sequences on the plasmid pKAT 102 (DSM 10031) or DNA sequences homologous therewith. The DNA sequences on pKAT 102 derive from *P. rubrum*. The DNA sequences are preferably selected from the nucleotide sequences shown in the sequence listings SEQ ID NO. 10–14 or nucleotide sequences hybridizing therewith. The DNA sequences present on the plasmid pKAT 102 are not identical to or closely related to those in the plasmids pKAT 101 and pSST 3001. The sequences found are homologous with regions of the csc operon from *E. coli* and with sequences from Gluconobacter or *Salmonella typhimurium*. FIG. 5 depicts the plasmid map of pKAT 102, indicating the sequenced part-sections. FIG. 6 shows a comparison of these sections with known bacterial regions homologous therewith.

The cell according to the invention with reduced sucrose metabolism may comprise the DNA sequence coding for a protein with a sucrose isomerase activity as a natural constituent of its chromosome. On the other hand, the cell may also be transformed with a sucrose isomerase gene. The sequences of sucrose isomerase genes from *Protaminobacter rubrum, Erwinia rhapontici*, Enterobacter species SZ 62 and *Pseudomonas mesoacidophila* MX-45 are described in PCT/EP 95/00165. These genes can be introduced into foreign prokaryotic or eukaryotic cells, resulting in cells which are transformed with a sucrose isomerase gene.

In one embodiment, this cell is a prokaryotic cell, preferably a Gram-negative prokaryotic cell, particularly preferably an enterobacterial cell. It is moreover possible on the one hand to use a cell which comprises no sucrose isomerase gene of its own, such as, for example, *E. coli*, but, on the other hand, it is also possible to use cells which already contain such a gene on their chromosome, for example the microorganisms mentioned above as source of sucrose isomerase genes. Preferred examples of suitable prokaryotic cells are *E. coli, Protaminobacter rubrum, Erwinia rhapontici*, Enterobacter spec. or *Pseudomonas mesoacidophila* cells. Transformation of prokaryotic cells with exogenous nucleic acid sequences is familiar to a skilled worker in the area of molecular biology (compare, for example, Sambrook et al., Supra, Chapter 1–4).

In another embodiment of the present invention, however, the cell according to the invention can also be a eukaryotic cell, such as, for example, a fungal cell (for example yeast), an animal or a plant cell. Methods for the transformation and transfection of eukaryotic cells with exogenous nucleic acid sequences are likewise familiar to the skilled worker in the area of molecular biology and need not be explained in detail here (compare, for example, Sambrook et al., Chapter 16).

It has also been possible, surprisingly, to identify sucrose metabolism mutants which produce the protein with sucrose isomerase activity constitutively, that is to say without addition of sucrose to the medium. In these cells there is preferably partial or complete deletion of the repressor of the scr operon.

Specific examples of sucrose metabolism mutants according to the invention are the *Protaminobacter rubrum* strains iiG Pr 20191 and iiG Pr 20710. Another example is the Enterobacter spec. Sz 62 strain iiG ES 2111 which was deposited at the DSM under deposit number DSM 10025. The *P. rubrum* mutant strains are able to produce 0.5 to 1.5 U/mg sucrose isomerase without addition of sucrose to the medium. By comparison with this, the *P. rubrum* wild-type strain produces only $\leq 0.1$ U/mg isomerase under identical conditions. The Enterobacter mutant strain displays the surprising property that it does not produce the sucrose isomerase on addition of sucrose to the medium. By contrast, addition of palatinose to the medium leads to production of the enzyme which is increased by comparison with the wild type. It appears that the sucrose uptake system is defective in this mutant, that is to say the cell is no longer able to take up sucrose and use it or a conversion product as inductor. A selective uptake system exists for palatinose, and either palatinose itself or a subsequent metabolic product thereof appears to act as inducer.

A preferred way of preparing sucrose defective mutants according to the invention comprises the identification, and partial or complete deletion, of genes which code for sucrose metabolizing enzymes in a particular organism. In many organisms this deletion is possible by introducing a vector which is suitable for homologous chromosomal recombination and which harbors a mutated sucrose metabolism gene, and selecting organisms in which such a recombination has taken place. The principle of selection by genetic recombination is explained in E. L. Winnacker, Gene und Klone, Eine Einführung in die Gentechnologie, VCH-Verlagsgesellschaft Weinheim, FRG, page 320 et seq.

Genes which code for sucrose metabolizing enzymes can be identified, on the one hand, by comparisons of homology with the nucleotide sequences disclosed in the present application and, on the other hand, by a selection method which is described hereinafter. In this selection method, the chromosomal DNA is isolated from a donor organism which contains genes coding for sucrose metabolizing enzymes, and is cleaved into fragments of the required size and introduced into a host organism which is itself unable to utilize sucrose. One example of a suitable host organism is *E. coli*. Colonies which contain genes coding for sucrose metabolizing enzymes can be identified by cultivation on McConkey sucrose medium and screening for red-colored colonies. In turn, those red-colored colonies identified in this way which are able to cleave sucrose to glucose and fructose are selected.

On the other hand, sucrose defective mutants can also be obtained by nonspecific mutagenesis from suitable starting organisms and selection of the sucrose defective mutants. When starting organisms with defects in palatinose metabolism are used it is possible to select for sucrose defective mutants by using McConkey sucrose media or minimal salt media with sucrose as sole C source. The mutants which are white on McConkey sucrose medium or which grow on minimal salt media with glucose as sole C source but not on corresponding media with sucrose as sole C source are identified as sucrose defective mutants. When other starting organisms are used it is expedient to use an additional selection marker, for example an antibiotic resistance gene.

The present invention thus also relates to a process for producing cells which comprise at least one DNA sequence coding for a protein with a sucrose isomerase activity and display a reduced sucrose metabolism, wherein at least one gene which codes for a sucrose metabolizing enzyme is inactivated by mutagenesis of the cell. This inactivation can take place, for example, by partial or complete deletion of the protein-encoding sequence or by partial or complete deletion of a regulatory sequence. The mutagenesis preferably takes place by introducing a vector which is suitable for homologous chromosomal recombination and which harbors a mutated DNA sequence which is essential for sucrose metabolism, and selecting cells in which such a recombination has taken place.

Another aspect of the present invention comprises cells which, besides a reduced sucrose metabolism, also display a reduced palatinose or/and trehalulose metabolism. Cells of this type produce even higher contents of the noncariogenic disaccharides trehalulose or/and palatinose, and diminished amounts of the interfering products glucose and fructose.

The term "reduced palatinose or/and trehalulose metabolism" means for the purpose of the present invention that a whole cell of the relevant organism produces acariogenic disaccharides on utilization of sucrose as C source but is able to utilize these metabolically to only a small extent, for example by degrading them to monosaccharides. The organism preferably produces less than 2.5%, particularly preferably less than 2%, most preferably less than 1% glucose plus fructose based on the total of acariogenic disaccharides and monosaccharide degradation products at a temperature of 15–65° C., in particular of 25–55° C.

In one embodiment of the present invention, the reduction in palatinose or/and trehalulose metabolism can take place by partial or complete inhibition of the expression of palatinase genes responsible for the intracellular degradation of palatinose or/and trehalulose. This inhibition of gene expression can take place, for example, by targeted mutation or/and deletion of the relevant genes. Specific examples of palatinase genes from *Protaminobacter rubrum* and *Pseudomonas mesoacidophila* are indicated in U.S. Pat. No. 5,786,140. This disclosure is incorporated herein by reference.

The organisms with reduced palatinose or/and trehalulose metabolism can furthermore be obtained by nonspecific mutagenesis from suitable starting organisms and selection of the corresponding defective mutants. One example of such a palatinase defective mutant is the *Protaminobacter rubrum* strain SZZ 13 which was deposited on Mar. 29, 1994, at the DSM under deposit number DSM 9121 in accordance with the provisions of the Budapest Treaty. This microorganism was produced by nonspecific mutagenesis of *P. rubrum* wild-type cells with N-methyl-N'-nitro-N-nitrosoguanidine and is distinguished in that it is no longer able to cleave the noncariogenic sugars trehalulose and palatinose to glucose and fructose. Selection of such mutants can take place, for example, by using MacConkey palatinose media or minimal salt media with palatinose or glucose as sole C source. The mutants which are white on MacConkey palatinose medium (Macconkey agar base from Difco Laboratories, Detroit, Mich. USA (40 g/l) and 10 g/l palatinose) or grow on minimal salt media with glucose as sole C source but not on corresponding media with palatinose as sole C source are identified as palatinase defective mutants.

An organism of this type with reduced palatinose or/and trehalulose metabolism can be used as starting organism for nonspecific mutagenesis in order to obtain a sucrose defective mutant.

The present invention furthermore relates to a process for preparing noncariogenic sugars, in particular trehalulose or/and palatinose, which is characterized in that the sugars are produced using (a) a cell which comprises at least one DNA sequence coding for a protein with a sucrose isomerase activity and displays a reduced sucrose metabolism, or/and (b) an extract from a cell of this type.

The process is generally carried out by cultivating the organism or the extract in a suitable medium under conditions such that sucrose is converted at least partially into acariogenic disaccharides by the sucrose isomerase. The acariogenic disaccharides are subsequently obtained from the medium or the organism and purified in a known manner.

In a preferred embodiment of this process, the organism or the extract is used in immobilized form. The immobilization of proteins (in pure form or in extracts) preferably takes place by coupling reactive side groups (for example NH$_2$ groups) to a suitable carrier. The immobilization of cells takes place, for example, in a sodium alginate/calcium chloride solution. A review of suitable methods for immobilizing cells and proteins is given, for example, by I. Chibata (Immobilized Enzymes, John Wiley and Sons, New York, London, 1978).

When a cell transformed with the sucrose isomerase gene is used it is possible to increase the rate of production of acariogenic sugars compared with known organisms by increasing the number of gene copies in the cell or/and by increasing the rate of expression in combination with strong promoters. It is furthermore possible, by transforming a cell which is unable or able to only a restricted extent to utilize acariogenic sugars with the sucrose isomerase gene, to produce a transformed cell which can be used to obtain acariogenic sugars, especially palatinose or/and trehalulose, without or with fewer by-products.

When a microorganism which already contains a functional sucrose isomerase gene is used, transformation with an exogenous sucrose isomerase gene is not essential but can be carried out to improve the yield.

The nucleic acids which code for enzymes of sucrose metabolism and which are disclosed in the present application, or partial fragments thereof, can be used to prepare mutagenesis vectors. These nucleic acids are preferably selected from one or more genes of bacterial scr or/and csc operons, for example from the genes scrK, scrY, scrA, scrB, scrR, hisD, gno, rafB, cscA and cscR, or fragments thereof. A nucleic acid which is particularly preferably used comprises (a) one or more of the nucleotide sequences depicted in SEQ ID NO. 1–14, (b) a sequence hybridizing with the sequences from (a) or/and (c) a fragment of one of the sequences from (a) or/and (b), where the length of the fragment is preferably at least 100 nucleotides.

The invention is furthermore described by the following sequence listings and figures:

SEQ ID NO. 1–3 show partial sequences from insertion of the plasmid PKAT 101 which comprise sections coding for sucrose metabolizing enzymes from P. rubrum, SEQ ID NO. 4–9 show partial sequences from insertion of the plasmid pSST 3001 which comprise regions coding for sucrose metabolizing enzymes from Enterobacter species SZ 62, SEQ ID NO. 10–14 show partial sequences of insertions of pXAT 102 which comprise regions coding for sucrose metabolizing enzymes from P. rubrum,

EXAMPLE 1

Isolation and characterization of scr genes for enzymes of sucrose metabolism from P. rubrum A gene bank was prepared from Protaminobacter rubrum complete DNA by use of Sau3AI partial digestion of the genome, obtaining collections of fragments about 10 kbp in size by elution of the fragments fractionated by gel electrophoresis, and ligation into a derivative of the λEMBL4 vector, λRESII (J. Altenbuchner, Gene 123, 63–68, 1993) which has been opened with BamHI. This was followed by transfection and conversion of the phages into plasmids in accordance with the above citation. The plasmids were introduced by transformation into E. coli cells. Subsequent screening took place for a red coloration of the kanamycin-resistant (25 μg/ml) cells on McConkey sucrose medium. Among the red-colored colonies sought, those whose crude extracts convert added sucrose into glucose and fructose are selected. This detection takes place, for example, via coupling of the reaction with glucose oxidase and detection of H$_2$O$_2$ formation, or by HPLC measurement. The plasmids isolated from these required clones confer on E. coli wild-type strains the ability to grow on minimal salt medium with sucrose as sole C source. The plasmids pKAT 101 and pKAT 103 were obtained in this way.

The sections of these plasmids which contain the genes which were sought were physically mapped by mutagenesis with a γδ insertion element (M. Strathmann et al., Proc. Natl. Acad. Sci. USA 88 (1991), 1247–1250). Plasmid mutants which no longer allow the cells to metabolize sucrose contain these insertion elements, which can be detected by restriction digestion, in certain sections of the P. rubrum DNA. Cleavage sites for the restriction enzyme SacI flank this region.

Figure 1:
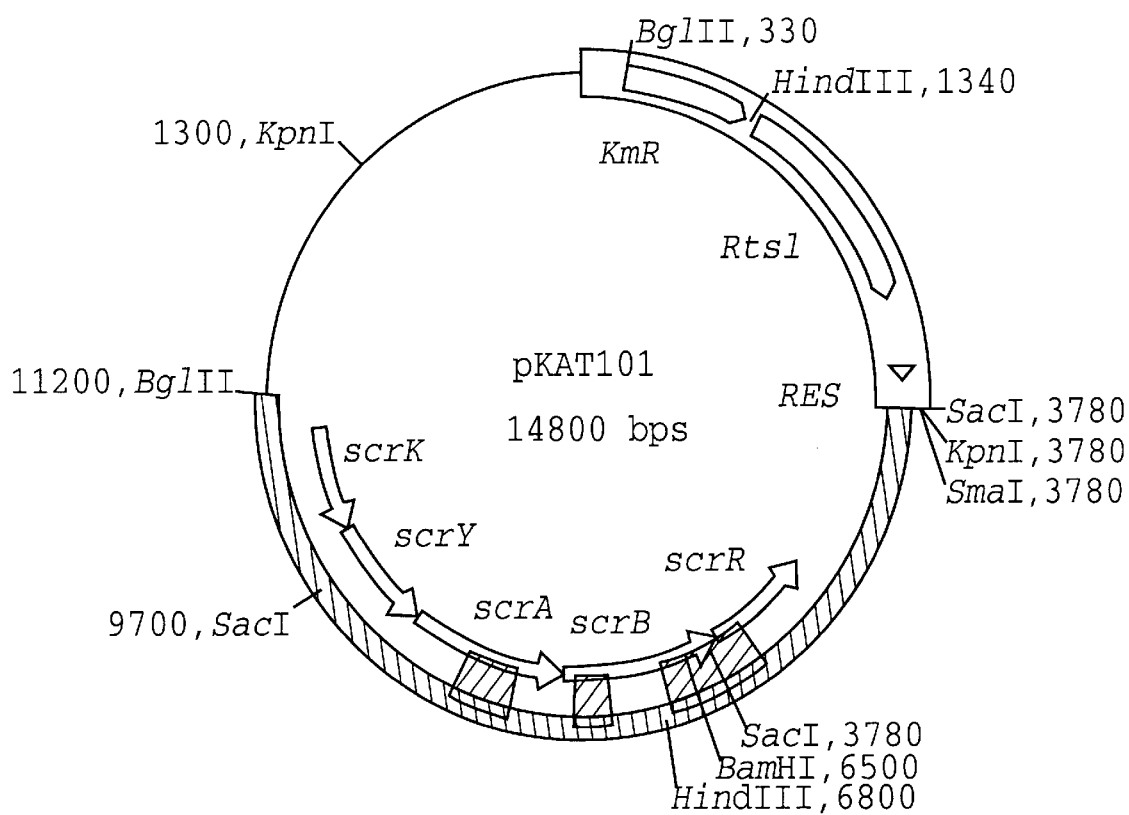
FIG. 1 and 2 show the plasmid maps of pKAT 101 and pKAT 103, indicating the sequenced part-sections.
Figure 2:
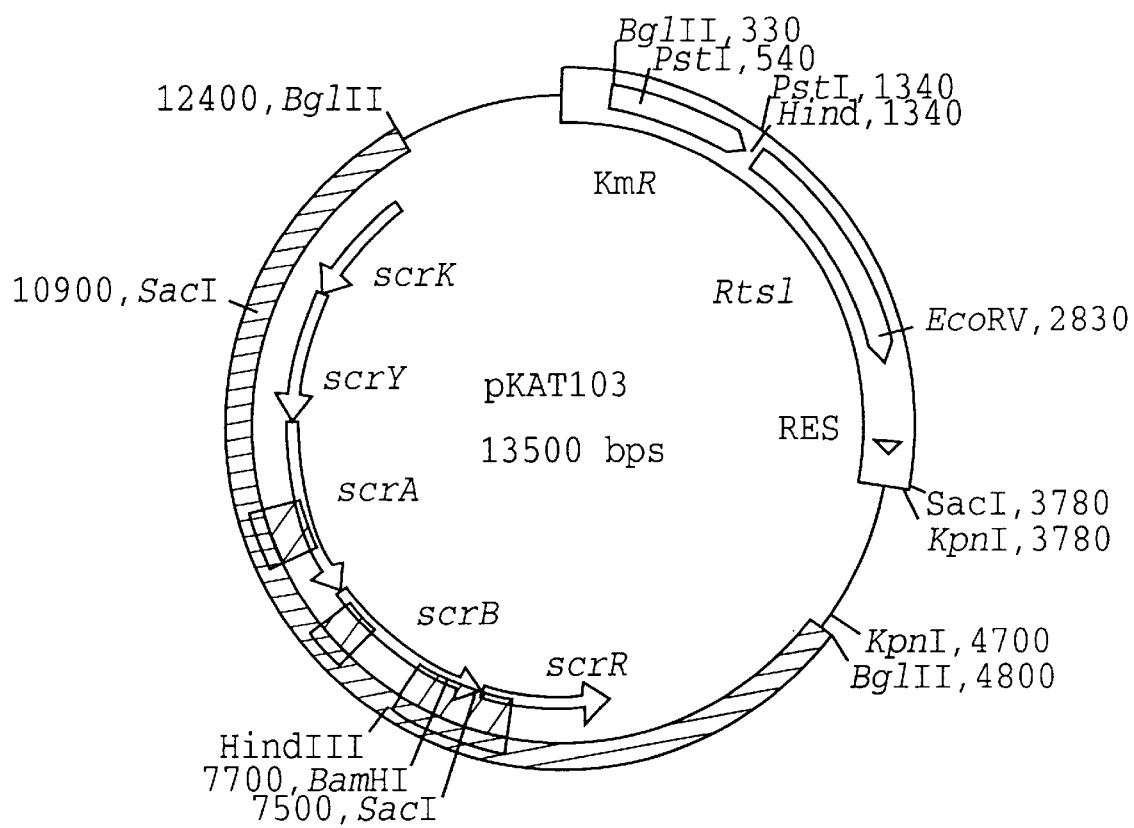
Figures 3A, 3B:
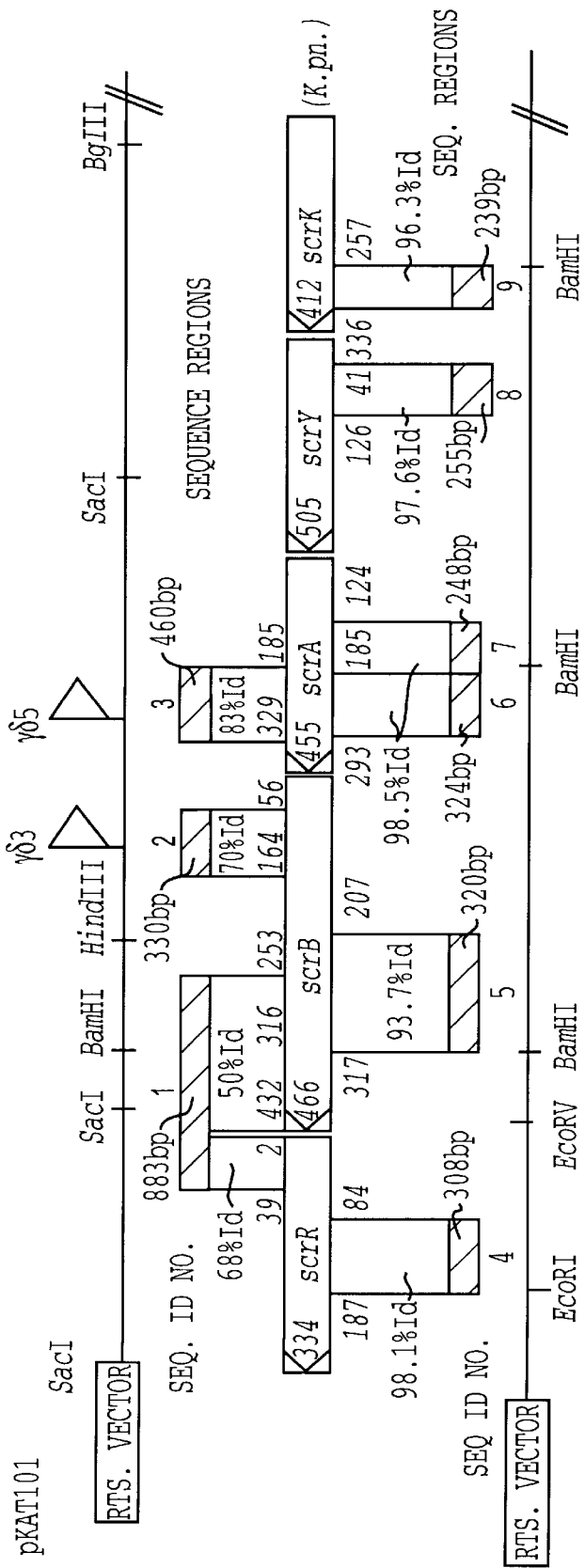
FIG. 3 shows a comparison of the sequenced part-sections from pKAT 101 and pSST 3001 with the regions, homologous therewith, from K. pneumoniae.

Partial fragments from this region of pKAT 101 were subcloned into M13 or pUC vectors, and the sequence of the cloned sections was determined by the Sanger method. Comparison of the sequence data obtained with those in the gene bank shows that the partial sequences found display a high degree of homology with regions of the scr regulon of Klebsiella pneumoniae (Jahreis, K. & J. W. Lengeler, Molecular Microbiology 9 195–209, 1993). The partial regions are, at the level of the translated sequence, 68–83% homologous with parts of the genes for scrR, scrB and scrA of the described organism. The corresponding sequence sections are referred to as SEQ ID NO. 1 (scrR-scrB), SEQ ID NO. 2 (scrB) and SEQ ID NO. 3 (scrA). FIGS. 1 and 2 depict the plasmid maps of pKAT 101 and pKAT 103, indicating the sequenced part-sections. FIG. 3a shows the homology of these sections with K. pneumoniae.

EXAMPLE 2

Isolation and characterization of the scr genes for enzymes of sucrose metabolism from Enterobacter spec. SZ 62

A gene bank was prepared from Enterobacter spec. SZ 62 complete DNA in E. coli in the same manner as described in Example 1. This gene bank was screened for red coloration of the kanamycin-resistant (25 μg/ml) cells on McConkey sucrose medium. Among the red-colored colonies sought, those whose crude extracts convert added sucrose into glucose and fructose are selected. The plasmids isolated from these required clones confer on *E. coli* wild-type strains the ability to grow on minimal salt medium with sucrose as sole C source. The plasmid pSST 3001 was obtained in this way.

Figure 4:
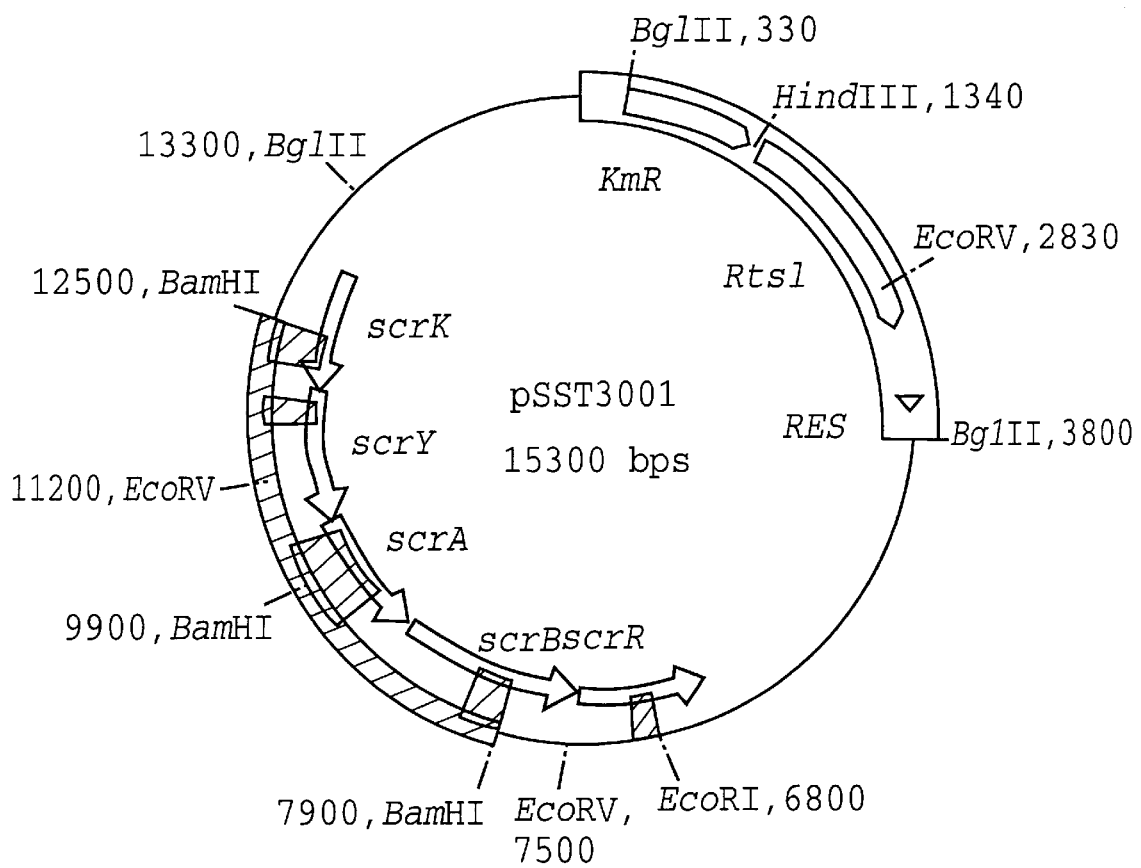
FIG. 4 shows the plasmid map of pSST 3001, indicating the sequenced part-sections.

Partial fragments from the insertion of pSST 3001 were subcloned in M13 or pUC vectors and sequenced. Comparison of the sequence data obtained with those in the gene bank shows that the partial sequences found display a high degree of homology with regions of the scr operon of *Klebsiella pneumoniae* (Jahreis and Lengeler, supra). The partial regions are, at the level of the translated sequence, 93–99% homologous with parts of the genes for scrb, scrA, scrY and scrK of the described organisms. The corresponding sequence sections are referred to as SEQ ID NO. 4 (scrR), SEQ ID NO. 5 (scrB), SEQ ID NO. 6 (scrA), SEQ ID NO. 7 (scrA), SEQ ID NO. 8 (scrY) and SEQ ID NO. 9 (scrK). Sequences are assigned to the homologous fragments from *K. pneumoniae* in FIG. 3*b*. It is evident that the known regions from Example 1 and Example 2 can be assigned to identical regions of the *K. pneumoniae* scr operon. A plasmid map of PSST 3001, indicating the sequenced regions, is depicted in FIG. 4.

EXAMPLE 3
Isolation and characterization of other genes for enzymes of sucrose metabolism from *P. rubrum*

The plasmid pKAT 102 was also obtained from the *P. rubrum* gene bank set up in Example 1. The genomic portions of this plasmid pKAT 102 are not identical to those of the plasmids pKAT 101 and pKAT 103. The sections of the plasmid pKAT 102 which contain the genes which were sought were determined by mapping with restriction endonucleases and deleting partial fragments. Plasmid mutants which no longer confer sucrose metabolism on the cells no longer contain these fragments detectable by restriction digestion.

Figure 5:
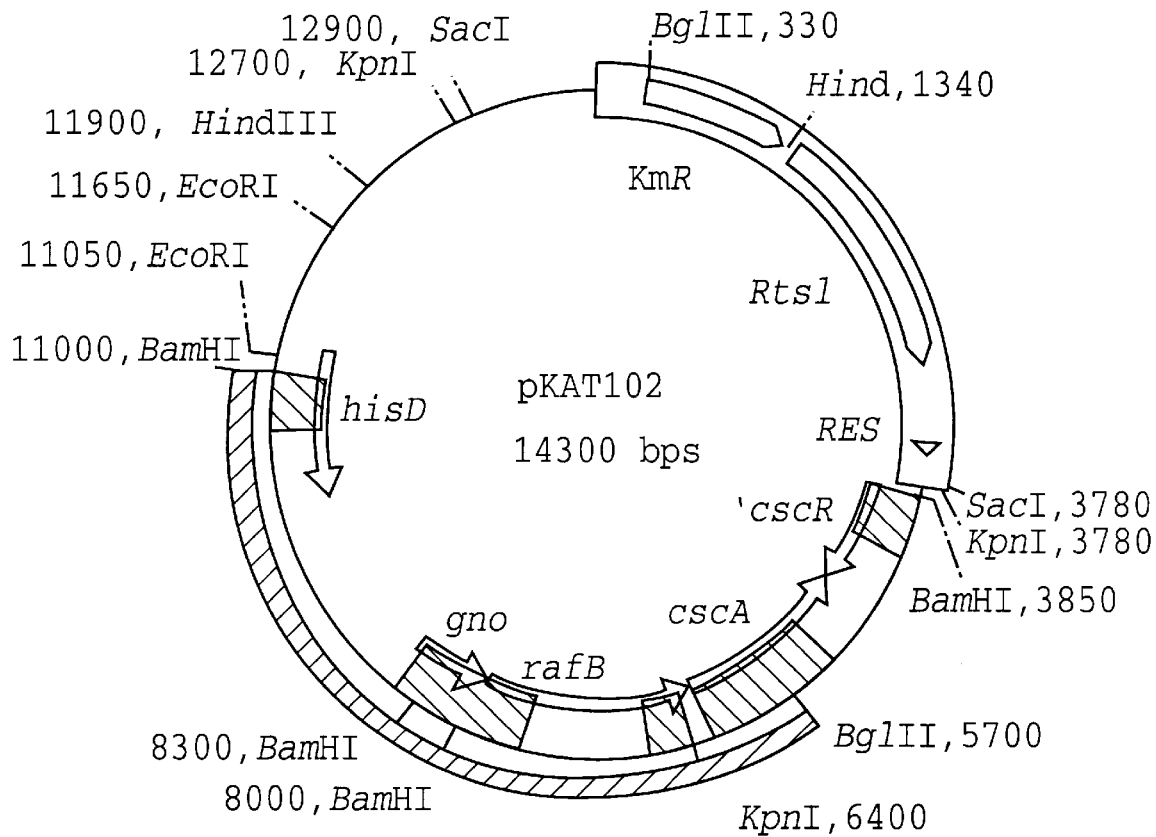
FIG. 5 shows the plasmid map of pKAT 102, indicating the sequenced part-sections

Partial fragments from the insertion of pKAT 102 were subcloned in M13 or pUC vectors and sequenced. The corresponding sequence sections are referred to as SEQ ID NO. 10 (cscR), SEQ ID NO. 11 (cscA), SEQ ID NO. 12 (rafB), SEQ ID NO. 13 (gno) and SEQ ID No. 14 (hisD). FIG. 5 depicts the plasmid map of pKAT 102.

Figure 6:
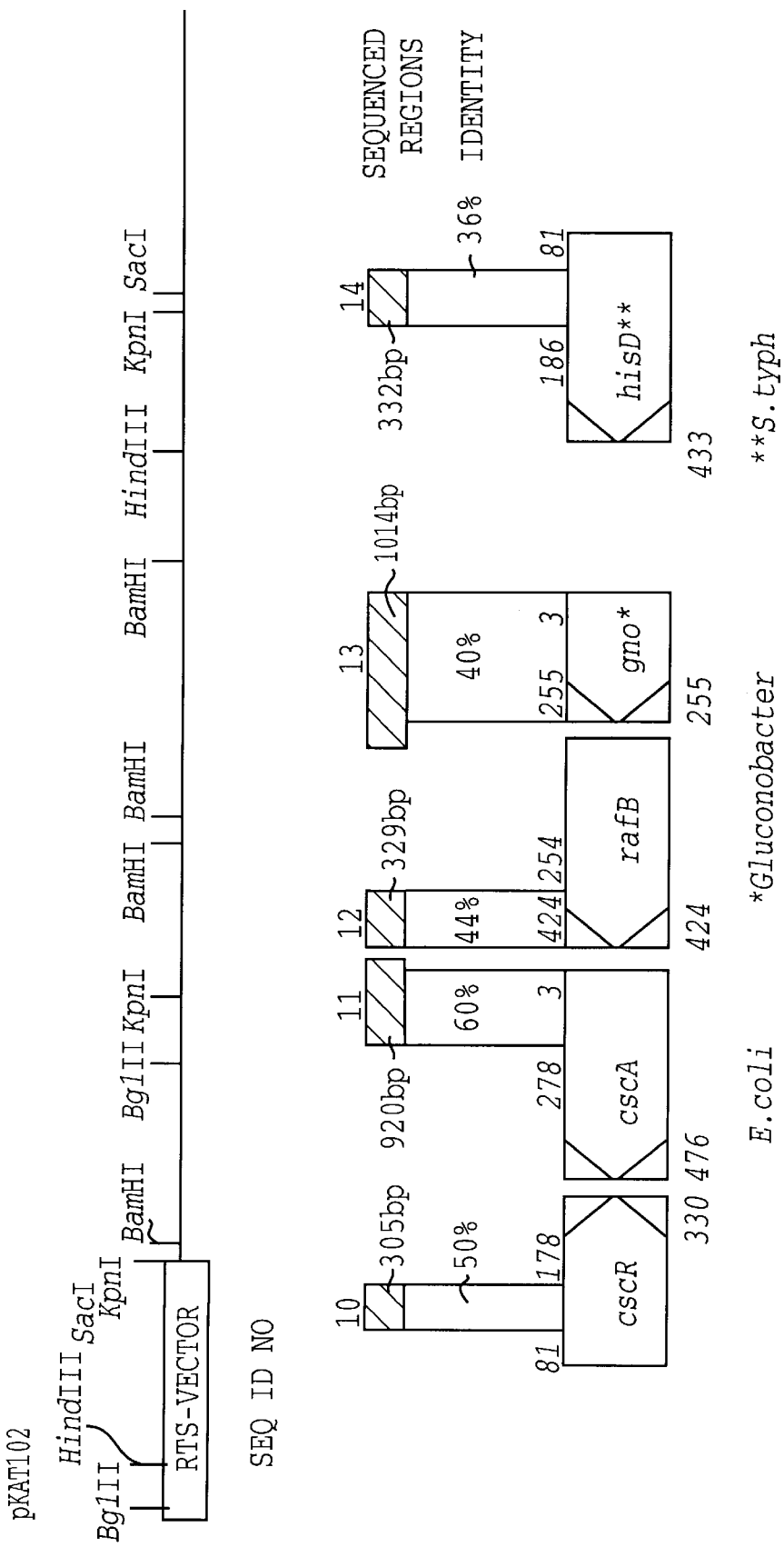
FIG. 6 shows a comparison of the sequenced part-sections from pKAT 102 with the regions, homologous therewith, from E. coli, Gluconobacter and Salmonella typhimurium.

These sequence sections are homologous with genes from the csc operon of *E. coli* (compare, for example, J. Bockmann et al., Mol. Gen. Genet. 235 (1992), 22–32) and with genes from Gluconobacter or *Salmonella typhimurium* (compare FIG. 6). cscA is in this connection an invertase gene and cscR is the repressor gene.

There are indications that csc genes are also present in Enterobacter spec. and can be inactivated in an analogous way.

EXAMPLE 4
Deletion of the scr genes for enzymes of sucrose metabolism in *P. rubrum*

The localization undertaken for the scr genes for the enzymes of sucrose metabolism on *P. rubrum* which are present on the plasmids pKAT 101 and PKAT 103 made it possible to establish the regions on the plasmids which flank these genes in the genome. Relative to the direction of reading of the genes (from the comparison with *K. pneumoniae*) there were isolated in each case a 5'-flanking fragment via KpnI-BglII from pKAT 101 and a 3'-flanking fragment via BglII-SacI from pKAT 103, which were connected via the BglII cleavage site in the vector pUC18. The plasmid pKAT 144 produced in this way thus contains the 5'- and 3'-flanking sequences without the portions which code for the enzymes of sucrose metabolism. Correspondingly, *E. coli* colonies which harbor pKAT 144 (ampicillin-resistant 50–100 µg/ml) are not red-colored on McConkey sucrose medium. These cells are also unable to grow on minimal salt medium with sucrose as sole C source. They therefore contain a deletion for the genes which encode the enzymes of sucrose metabolism compared with cells with pKAT 101 or pKAT 103.

In addition, a gene cassette coding for chloramphenicol acetyltransferase (cat) was introduced into the unique BglII cleavage site of pKAT 144. This gene cassette is derived from the plasmid pBR 328 (Soberon et al., Gene 9 (1980), 287) which is commercially obtainable from Boehringer Mannheim. Cleavage of this plasmid with AatII and SauI resulted in a 1.5 kb fragment which, after treatment of the ends with Klenow enzyme, is available for insertion into vector plasmids. The plasmid pKAT 151.1 which additionally confers resistance to chloramphenicol ($Cm^R$, 25–50 µg/ml) on the cell was obtained in this way.

Introduction of this 5'-3' fragment from pKAT 144 or pKAT 151.1 into a pUT vector (Herrero, M. de Lorenzo, V., Timmis, K. N. J., Bacteriology 172: 6557–6567, 1990) results in pUT plasmid derivatives pKAT 150.1 and pKAT 154.1 ($Cm^R$), respectively, which can now be established and replicated only in suitable *E. coli* host cells which make the Pir protein available. Suitable for this purpose are the *E. coli* strains CC118λpir⁺ (Herrero, M., de Lorenzo, V., Timmis, K. N. J., Bacteriology 172: (11) 6557–6567, 1990) or S17-1λpir⁺ (de Lorenzo, V., Timmis, K. N., in Methods in Enzymology 235: 386–405, 1994). The latter strain is able to mobilize the pUT plasmid derivatives. When recipient bacteria are crossed with this donor strain, the corresponding pUT plasmid derivative is transferred. If the recipient bacteria do not produce the Pir protein, the transferred plasmid is not capable of replication and is lost. However, if there is a homology between the sequences on the pUT plasmid derivative and the chromosomal DNA of the recipient bacterium, it is possible for there to be recombinant integration of the pUT plasmid derivative into the chromosomal DNA of the recipient bacterium. This event is associated with integration of the resistance genes of the pUT plasmid derivative into the chromosomal DNA of the recipient bacterium.

The pUT plasmid derivatives used harbor either the gene for resistance to ampicillin (pKAT150.1) or the gene for ampicillin resistance and, in addition, the gene for resistance to chloramphenicol (pKAT 154.1). Preferably used as recipients are rpoB mutants of the *P. rubrum* strain (iiG Pr2) which are resistant to rifampicin (50–100 µg/ml). This makes it possible selectively to eliminate the *E. coli* donor bacteria, S17-1λpir⁺. The required exconjugants are obtained as resistant to ampicillin (100 µg/ml) and rifampicin (50–100 µg/ml) on agar plates with nutrient broth after incubation at 30° C. for 18–36 hours and are purified to single colonies. A single colony obtained in this way is inoculated in nutrient broth without added antibiotic at 30° C. and cultivated overnight. The resulting culture is plated in a suitable dilution series on McConkey sucrose medium. The single colonies produced after incubation at 30° C. overnight are, in 20–60% of cases, no longer red-colored, in contrast to the *P. rubrum* control bacteria used, which had not been crossed with the *E. coli* cells. The cells which are not red-colored are no longer resistant to ampicillin. These cells are also unable to grow on minimal salt medium with sucrose as sole C source. However, they are still resistant to rifampicin and, accordingly, are sucrose metabolism defective mutants of *P. rubrum* (strain iiG Pr 20191). When the pUT plasmid derivative pKAT 154.1 into which the Cm$^R$ gene has additionally been introduced is used, it is also possible and expedient to add chloramphenicol (25–50 μg/ml) at each stage of selection (strain iiG Pr 20710).

The *P. rubrum* scr mutants obtained in this way, for example iiG Pr 20191 and iiG Pr 20710, display the surprising property that they now produce the sucrose mutase enzyme constitutively, 0.5–1.5 U/mg, that is to say without adding sucrose to the medium. By comparison with this, the wild-type *P. rubrum* produces only ≦0.1 U/mg without sucrose in the medium.

An invertase activity can still be detected in the mutants obtained in this way after culturing with sucrose. Thus, besides the characteristic scr operon there is also at least one other gene or a group of genes for enzymes of sucrose metabolism present in *P. rubrum*, which is proven by the isolation of pKAT 102, Example 3. However, these genes (cloned on pKAT 102) are insufficient on their own to make the described *P. rubrum* scr mutants able to grow on sucrose as sole C source.

Since the mutase activity is now constitutively produced in the mutants, culturing without added sucrose in the medium is possible. It is advantageous in this connection that these mutants have no enzyme activity which converts sucrose apart from the mutase. This results in cells which are more suitable for producing palatinose.

EXAMPLE 5
Deletion of the scr genes for enzymes of sucrose metabolism in Enterobacter spec. SZ 62 The localization undertaken for the genes for the enzymes of sucrose metabolism on Enterobacter spec. SZ 62 which are present on the plasmid pSST 3001 made it possible to establish the regions on the plasmid which flank these genes in the genome. Deletion of two BamHI fragments, 2.0 and 2.6 kbp in size, by digestion of pSST 3001 with this enzyme and religation resulted in the plasmid pIV1. This plasmid thus contains the 5'- and 3'-flanking sequences without the portions which code for the enzymes of sucrose metabolism. Correspondingly, *E. coli* colonies which harbor pIV1 (kanamycin-resistant, 25–50 μg/ml) are not red on McConkey sucrose. These cells are also unable to grow on minimal salt medium with sucrose as sole C source. They therefore contain a deletion in the region of the genes which code for enzymes of sucrose metabolism compared with cells with pSST 3001. In addition, a gene cassette coding for chloramphenicol acetyltransferase (cat) can be introduced into the unique BamHI cleavage site of pIV1. This results in the plasmid pIV3 which additionally confers resistance to chloramphenicol (Cm$^R$, 25–50 μg/ml) on the cell.

Insertion of the 5'-3' fragment from pIV3 into a pUT vector in accordance with Example 4 results in the pUT plasmid derivative pIV4(Cm$^R$) which can row be established and replicated only in suitable *E. coli* host cells which make the Pir protein available. Suitable for this purpose are the *E. coli* strains CC118λpir$^+$ or S17-1λpir$^+$.

The pUT plasmid derivative pIV4 harbors the gene for resistance to ampicillin and, in addition, a gene for resistance to chloramphenicol. It is expedient to use as recipients gyrA mutants of the Enterobacter spec. SZ62 strain (iiG Es 2) which are resistant to nalidixic acid (Nal$^R$, 30–50 μg/ml). This makes it possible selectively to eliminate the *E. coli* donor bacteria S17-1λpir$^+$. The required exconjugants are obtained as resistant to ampicillin (100 μg/ml) and nalidixic acid (30–50 μg/ml) on agar plates with nutrient broth after incubation at 37° C. for 18–36 hours and are purified to single colonies. A single colony obtained in this way is inoculated in nutrient broth without added antibiotic at 37° C. and cultivated overnight. The resulting culture is plated in a suitable dilution series on McConkey sucrose medium. The single colonies resulting after incubation at 37° C. overnight are in 20–60% of cases no longer red-colored, in contrast to the Enterobacter spec. SZ62 control bacteria used, which had not been crossed with the *E. coli* cells. The cells which are not red-colored are no longer resistant to ampicillin. These cells are also unable to grow on minimal salt medium with sucrose as sole C source. However, they are still resistant to nalidixic acid and, accordingly, are sucrose metabolism defective mutants of Enterobacter spec. SZ 62. When the pUT plasmid derivative pIV4 to which the Cm$^R$ gene has additionally been introduced is used, it is possible and expedient also to add chloramphenicol (25–50 μg/ml) at each stage of the selection (strain iiG Es 2111, DSM 10025).

The obtained Enterobacter spec. SZ62 scr mutants display the surprising property that they now do not produce the sucrose mutase enzyme on addition of sucrose to the medium. By contrast, addition of palatinose to the medium leads, as also in the wild type, to production of the enzyme in a yield of 0.5–1.5 U/mg. The cells cultured with palatinose in place of sucrose in the medium show, on conversion of sucrose into palatinose, a distinctly diminished formation of saccharides such as glucose and fructose; the palatinose yield of the mutants is in this case increased from 59% to 71.9% (see Table 1).

TABLE 1

| | | | Product composition in % | | | | |
|---|---|---|---|---|---|---|---|
| | Mutase mU/mg | Invertase mU/mg | Glucose | Fructose | Trehalulose | Palatinose | Sucrose |
| Culturing with sucrose | | | | | | | |
| iiG Es 2 | 593 | 190 | 8.7 | 8.1 | 17.3 | 61.7 | 4.1 |
| iiG EG 2111 | 0 | 171 | 23.4 | 29.3 | 0 | 0 | 47.3 |
| Culturing with palatinose | | | | | | | |
| iiG Es 2 | 339 | 99.3 | 8.7 | 9.4 | 16.0 | 59.1 | 7.7 |
| iiG Es 2111 | 621 | 36.1 | 1.3 | 1.5 | 19.5 | 71.9 | 5.8 |

EXAMPLE 6
Deletion of the csc genes for enzymes of sucrose metabolism in *P. rubrum*

*P. rubrum* sucrose deletion mutants were produced by the method described in Example 4 starting from the plasmid pKAT 102.

There were isolated in each case from pKAT 102 a 5'-flanking fragment via SacI-BamHI digestion and a 3'-flanking fragment via KpnI-BglII digestion (see FIG. 5), and these were inserted via the BamHI-BglII cleavage sites into the pUC18 vector. This resulted in the plasmid pSKAT9. Alternatively, these fragments were linked via the cat cassette described in Example 4 and inserted into pUC18. This resulted in the plasmid pSKAT8. It is possible to obtain from these plasmids pSKAT9 and pSKAT8 the 5'-3' deletion cassettes for csc genes from *P. rubrum* in accordance with Example 4 by SacI/BamHI and HindIII digestion, respectively, and they can be inserted into a pUT vector. The subsequent procedure was as described in Example 4.

The mutants with deletions in csc genes also have improved properties compared with the initial cells in the sense that they show an increased palatinosetrehalulose yield and produce fewer unwanted mono- and oligosaccharides as by-products.

EXAMPLE 7

Preparation of a *Protaminobacter palatinase* defective mutant

Cells of *Protaminobacter rubrum* (CBS 547, 77) were mutagenized with N-methyl-N'-nitro-N-nitrosoguanidine by the method of Adelberg et al. (Biochem. Biophys. Research Commun. 18 (1965), 788) modified by Miller, J., Experiments in Molecular Genetics, Cold Spring Harbor Laboratory, 125–179 (1972). Palatinase defective mutants were selected using MacConkey palatinose medium (MacConkey agar base) Difco Laboratories, Detroit, Mich., USA), 40 g/l with the addition of 20 g/l palatinose, sterilized by filtration, 25 mg/l kanamycin) and minimal salt media (10.5 g $K_2HPO_4$, 4.5 g $KH_2PO_4$, 1 g $(NH_4)_2SO_4$, 0.5 g sodium citrate. 2 $H_2O$, 0.1 g $MgSO_4.7H_2O$, 1 mg thiamine, 2 g palatinose or glucose, 25 mg kanamycin and 15 g agar per liter, pH 7.2). Mutants of *P. rubrum* which are white on McConkey palatinose medium or grow on minimal salt medium with glucose in contrast to the same medium with palatinose are identified as palatinase defective mutants. The enzyme activity of cleaving palatinose to glucose and fructose (palatinase activity) cannot be detected in cell extracts from the mutants, in contrast to the wild type. When these cells are cultured in minimal salt medium with 0.2% sucrose as sole C source, in contrast to the wild-type cells with which palatinose can be detected only transiently in the time from 4 to 11 hours after the start of culturing, a persistent accumulation of palatinose (isomaltulose) is detectable. Overnight cultures in the same medium contain no palatinose in the ease Of wild-type cells but curltains >0.08% palatinose in the case of the mutant SZZ 13 (DSM 9121) prepared in this way.

*P. rubrum* sucrose deletion mutants were produced by the methods described in Examples 4 and 6 starting from the palatinose deletion mutant SZZ 13 and the plasmids pKAT 101, pKAT 103 and pKAT 102.

These deletion mutants which, besides a defect in sucrose metabolism, display an additional defect in palatinose metabolism also show improved properties in the production of palatinose/trehalulose compared with the initial cells (*P. rubrum* wild type and mutant SZZ 13).

EXAMPLE 8

Immobilization of microorganism cells

Cells are rinsed off a subculture of the appropriate strain using 10 ml of a sterile nutrient substrate consisting of 8 kg of fig juice from a sugar factory (dry matter content=65%), 2 kg of corn steep liquor, 0.1 kg of $(NH_4)_2HPO_4$ and 89.9 kg of distilled water, pH 7.2. This suspension is used as inoculum for the preculture in 1 l flasks containing 200 ml of nutrient solution of the above composition in a shaker. After incubation at 29° C. for 30 hours, 10 flasks (total content 2 l) are used to inoculate 18 l of nutrient solution of the above composition in a 30 l small-scale fermenter, and fermentation is carried out at 29° C. introducing 20 l of air per minute and stirring at 350 rpm.

After the bacterial counts have reached more than $5 \times 10^9$ bacteria per ml, the fermentation is stopped and the cells are harvested from the fermenter solution by centrifugation. The cells are then suspended in a 2% strength sodium alginate solution and immobilized by dropwise addition of the suspension to a 2% strength calcium chloride solution. The resulting immobilizate beads are washed with water and can be stored at +4° C. for several weeks.

Cells of sucrose metabolism mutants prepared as in Examples 4 to 6 show better catalytic properties in respect of their product composition than do comparable cells from the known microorganisms *Protaminobacter rubrum* (CBS 547,77) *Erwinia rhapontici* (NCPPB 1578) and Enterobacter species.

---

We claim:

1. An isolated cell which comprises at least one DNA sequence coding for a protein with a sucrose isomerase activity wherein sucrose is isomerized to palatinose andor trehalulose wherein the cell displays a reduced sucrose metabolism.

2. The isolated cell according to claim 1, wherein the reduction in sucrose metabolism takes place by partial or complete inhibition of the expression of at least one gene which codes for a sucrose metabolizing enzyme.

3. The isolated cell according to claim 1, wherein the reduction in sucrose metabolism takes place by partial or complete inhibition of the expression of DNA sequences on the plasmids pKAT 101 (DSM 10030) or pKAT 103 (DSM 10032) or DNA sequences hybridizing therewith.

4. The isolated cell according to claim 3, wherein the DNA sequences are selected from the nucleotide sequences shown in SEQ ID No. 1–3 or nucleotide sequences hybridizing therewith, wherein a positive hybridization signal is still observed after washing with 1×SSC and 0.1% SDS at 55° C. for one hour.

5. The isolated cell according to claim 1, wherein the reduction in sucrose metabolism takes place by partial or complete inhibition of the expression of DNA sequences on the plasmid pSST 3001 (DSM 10033) or DNA sequences hybridizing therewith.

6. The isolated cell according to claim 5, wherein the DNA sequences are selected from the nucleotide sequences shown in SEQ ID NO. 4–9 or nucleotide sequences hybridizing therewith, wherein a positive hybridization signal is still observed after washing with 1×SSC and 0.1% SDS at 55° C. for one hour.

7. The isolated cell according to claim 1, wherein the reduction in sucrose metabolism takes place by partial or complete inhibition of the expression of DNA sequences on the plasmid pKAT 102 (DSM 10031) or DNA sequences hybridizing therewith, wherein a positive hybridization signal is still observed after washing with 1×SSC and 0.1% SDS at 55° C. for one hour.

8. The isolated cell according to claim 1, wherein the DNA sequence is selected from the nucleotide sequences shown in SEQ ID NO. 10–14 or nucleotide sequences hybridizing therewith, wherein a positive hybridization signal is still observed after washing with 1×SSC and 0.1% SDS at 55° C. for one hour.

9. The isolated cell according to claim 1, wherein it is transformed with a sucrose isomerase gene.

10. The isolated cell according to claim 1, wherein it is a prokaryotic cell.

11. The isolated cell according to claim 10, wherein it is a Gram-negative prokaryotic cell.

12. The isolated cell according to claim 10, wherein it is an enterobacterial cell.

13. The isolated cell according to claim 10, wherein it is an *Escherichia coli, Protaminobacter rubrum, Erwinia rhapontici, Pseudomonas mesoacidophila* or Enterobacter spec. cell.

14. The isolated cell according to claim 1, wherein it constitutively produces the protein with a sucrose isomerase activity.

15. The isolated cell according to claim 14, wherein the repressor of the scr operon is partially or completely deleted.

16. Enterobacter spec. SZ 62 mutant iiG Es 2111 (DSM 10025).

17. The isolated cell according to claim 1, wherein it furthermore displays a reduced palatinose or/and trehalulose metabolism, wherein the reduced palatinose or/and trehalulose metabolism occurs in a cell producing less than 2.5% glucose plus fructose based on the total of acariogenic disaccharides and monosaccharide degradation products at a temperature of 15–65° C.

18. The isolated cell according to claim 17, wherein the reduction in palatinose or/and trehalulose metabolism takes place by partial or complete inhibition of palatinase or/and trehalulase genes.

19. A process for producing cells which display a reduced sucrose metabolism comprising inactivating by mutagenesis of the cell at least one gene which codes for a sucrose metabolizing enzyme, wherein said cells comprise at least one DNA sequence coding for a protein with a sucrose isomerase activity wherein sucrose is isomerized to palatinose and/or trehalulose.

20. The process according to claim 19, wherein the mutagenesis takes place by introducing a vector which is suitable for homologous chromosomal recombination and which harbors a mutated DNA sequence which is essential for sucrose metabolism, further comprising selecting cells in which such a recombination has taken place.

21. A process for producing noncariogenic sugars comprising incubating the cell according to claim 1 and/or an extract from the cell according to claim 1 in a suitable medium under conditions such that sucrose is isomerized into noncariogenic disaccharides.

22. The process according to claim 21, wherein the cell or the extract is used in immobilized form.

23. A method for producing a mutagenesis vector suited for homologous chromosomal recombination comprising inserting in a vector, a nucleic acid which codes for a mutant enzyme of sucrose metabolism.

24. The method according to claim 23, wherein the nucleic acid is selected from one or more genes of bacterial scr or/and csc operons.

25. The method according to claim 24, wherein the nucleic acid comprises:
(a) one or more of the nucleotide sequences depicted in SEQ ID NO. 1–14
(b) a sequence hybridizing with the sequences from (a), wherein a positive hybridization signal is still observed after washing with 1×SSC and 0.1% SDS at 55° C. for one hour, or/and
(c) a fragment of one of the sequences from (a) or/and (b) wherein the length of the fragment is at least 100 nucleotides.

26. A plasmid selected from the group consisting of pKAT 101 (DSM 10030), pKAT 102 (DSM 10031), pKAT 103 (DSM 10032), and pSST 3001 (DSM 10033), wherein the plasmid comprises at least one DNA sequence coding for a sucrose isomerase activity.

27. The process of claim 21 wherein the sugar is palatinose.

28. The process of claim 21 wherein the sugar is trehalulose.

29. The process of claim 21 wherein a cell is used to produce the sugars.

30. The process of claim 21 wherein an extract from a cell is used to produce the sugars.

* * * * *

UNITED STATES PATENT AND TRADEMARK OFFICE
CERTIFICATE OF CORRRECTION

PATENT NO. : 5,985,668
DATED : 11/16/99
INVENTOR(S) : Mattes et al.

It is certified that error appears in the above-identified patent and that said Letters Patent is hereby corrected as shown below:

On the title page: Item [56] insert the following:

FOREIGN PATENT OR PUBLISHED FOREIGN PATENT APPLICATION

| | | DOCUMENT NUMBER | PUBLICATION DATE | COUNTRY OR PATENT OFFICE | CLASS | SUBCLASS | TRANSLATION YES | NO |
|---|---|---|---|---|---|---|---|---|
| | | EP 0 483 755A2 | 05/06/92 | EUROPE | | | X | |
| | | EP O 509 834A2 | 10/21/92 | EUROPE | | | X | |

OTHER DOCUMENTS (Including Author, Title, Date, Pertinent Pages, ETC.)

| | |
|---|---|
| | Brückner, Reinhold, et al., "Characterization of a Sucrase Gene from Staphylococcus Xylosus," *J.* of Bacteriology, Feb. 1993, p. 851-857 |
| | Sprenger, G.A., et al., "Analysis of Sucrose Catabolism in *Klebsiella pneumoniae* and in Scr+ Derivatives of Escherichia *coli* K12," *J. of General Microbiology* (1988), 134, 1635-1644. |
| | European Patent Office Search Report for EP 96 110396, dated 22 April 1999. |

Signed and Sealed this

Fifth Day of September, 2000

Attest:

Attesting Officer

Q. TODD DICKINSON

*Director of Patents and Trademarks*

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
      (A) LENGTH: 863 base pairs
      (B) TYPE: nucleic acid
      (C) STRANDEDNESS: both
      (D) TOPOLOGY: linear (ii) MOLECULE TYPE: DNA (genomic)

(vi) ORIGINAL SOURCE:
      (A) ORGANISM: Protaminobacter rubrum (xi) SEQUENCE DESCRIPTION: SEQ ID NO: 1:

```
ATGAACGTTA TCTCAACGTT TAVCCAGRCG GGCTATCTGA CCGGCACGCT GGATTATCGA      60

CAGGCGGCCT TTGAACATGG CGAATTCCAC GAGCTGGACG CCGGGTTCGA ATTCTATGCG     120

CCGCAAACCA CGCTGCCGAA GACGGCCGCC GCCTGCTGGT CGGCTGGATG GGCGTACCGG     180

AGCAGGACGA AGTCTGTCAC CCGACGTTGC AATACGGCTG GATCCATACC ATGACCTGCC     240

CGCGCGAACT TTCTTTGCAG AACGGCAAGC TTTACCAGCA GCCGGCGCGC GAGCTGCAAC     300

GCGTGCGCGG CGAGGGCAGC CAATGGCAGG GAATGGCGGG TAACGCCCCT GTCTGGCCGG     360
```

```
TCGACAGTGC CGAAGTGTTG TTGACGCCCA ACGGCGCATT CAGCGCCGAC TTTGGCGATG      420

CGATGACGCT GAGCTGGGAC GGCGCCTTGC TGCGTCTGAC GCGCAACAAC CTGCGCAACG      480

GGCAGCCTGA ACACCGTTAC TGGCGCGGTG AGGTCACCCA TCTGCAAATG CTGTTCGACA      540

GCTCCAGCGT GGAGATTTTT ATCAACCACG GCGAAGGGGT CATGAGCTCA CGCTACTTCC      600

CTGGCCCGCA ACCGTTGCTG CGTTTGAGCG GTGAGACGCA GCTTGCACTG GAGCACTGGC      660

CGCTGACGCC ATGCATGCTA GAATGACGCA TCTCCCGTTG AACTCAGATG CCGCCAGGTG      720

AAAAAAAACA AACGATAACC ATCAGTGATA TTGCCGCGCT GGCCGGCGTG TCGAAATCGA      780

CCGCCAGCCT GGTGCTTAAC GGACGCAGCA AGAATATCG GGTGTCCGAC GACACGTGAC       840

GTATCTGCGC TGGCGGCGAG CAC                                             863

(2) INFORMATION FOR SEQ ID NO: 2:

(i) SEQUENCE CHARACTERISTICS:
        (A) LENGTH: 329 base pairs
        (B) TYPE: nucleic acid
        (C) STRANDEDNESS: both
        (D) TOPOLOGY: linear (ii) MOLECULE TYPE: DNA (genomic)

(vi) ORIGINAL SOURCE:
        (A) ORGANISM: Protaminobacter rubrum (xi) SEQUENCE DESCRIPTION: SEQ ID NO: 2:

TCTATCAGTG GAACCCGCTG GGCTGCGATC ACCGCAACAA ATGCTGGGGC CATTGGCAAT       60

CGACGGATCT GCTCAACTGG CAGCATCAGC CGGTGGCGCT GGTGCCCGGC GCTTGTTACG      120

ACAGSCASGG CTGTTACTCA GGCTCGGCGG TGGTGGCAGA CGGCAAAATC ATGCTGGCGT      180

ATACCGGCAA CGTAAAATAC CCCGACGGTT CTCGCACAGC GTACCAGTGC CTGGCGYYGG      240

AAAATGCGCA GGGCGGGTAT GACAAGCTCG GCCCGGTGCT GCCGCTGCCG GAAGCTACAG      300

CGGCCACGTG CGCGATCCNA AGGTTTGGC                                       329

(2) INFORMATION FOR SEQ ID NO: 3:

(i) SEQUENCE CHARACTERISTICS:
        (A) LENGTH: 465 base pairs
        (B) TYPE: nucleic acid
        (C) STRANDEDNESS: both
        (D) TOPOLOGY: linear (ii) MOLECULE TYPE: DNA (genomic)

(vi) ORIGINAL SOURCE:
        (A) ORGANISM: Protaminobacter rubrum (xi) SEQUENCE DESCRIPTION: SEQ ID NO: 3:

GATTATTGGC CATCGACCAG ATCGGCAGCC AGGAAGTTAA CGCCGATTTC CGGGTTGCCG       60

AGCAGCCCCC CCTCTACGGC GTGGAAGCTG TGGTGAATGC CGGTGATGAC GATGGCGGAA      120

TACAGGCCGC CGAACAGGAA TCCGGCGAAC CAACCGGCGT GGGCAATCAG CGTGCTGAGC      180

ACGAAGGAGA TGCCGTCACC CAGTGTGCGC CCGGCGGGGC CGATAAACAG CATGGCGACG      240

AAGCCGGAGA TCACCACCGT CAGGAATGGC GTCAGGATCA GGTCCAGCGC GTTGGGGATC      300

ACTCTGCGCA GCTGTTTTTC CAGCACGCTC ATAAACCACA CCGTCAGCAG CACCGGGAAC      360

ACCGTACCCT GATAGCCGAT CATGGCGATA TCGAGTCCGA AGAAATTCAT GGTGTGGAAA      420

CCGCCCGCGA CGCCCCAGGC GTTGGTCAGC GCCGGGTGAG TCAGG                     465
```

(2) INFORMATION FOR SEQ ID NO: 4:

(i) SEQUENCE CHARACTERISTICS:
        (A) LENGTH: 308 base pairs
        (B) TYPE: nucleic acid
        (C) STRANDEDNESS: both
        (D) TOPOLOGY: linear (ii) MOLECULE TYPE: DNA (genomic)

(vi) ORIGINAL SOURCE:
        (A) ORGANISM: Enterobacter species (xi) SEQUENCE DESCRIPTION: SEQ ID NO: 4:

```
TTTTCTCCCA TGAGCTTGAG ACGCTCTGCC GGGAAGCTGG BGKGCAGCTG CTTATCTCCT      60

GCACCGACGA AAACCCCGGC CAGGAGAGCG TGGTGGTCAA TAATATGATT GCCCGCCAGG     120

TCGACGGGCT GATCGTCGCC TCGTGCATGC ACAGCGATGC CGACTACCTG AAGCTCAGCG     180

AACAGCTGCC GGTGGTGCTT TTTGACCGCT CCCCCAGCGA CAGCGCCCTG CCGCTGGTGA     240

TGACCGACTC GGTGACGCCA ACCGCCGAGC TGATCTCCCG CATTGCGCCT CAGCATGCGG     300

ACGAATTC                                                              308
```

(2) INFORMATION FOR SEQ ID NO: 5:

(i) SEQUENCE CHARACTERISTICS:
        (A) LENGTH: 335 base pairs
        (B) TYPE: nucleic acid
        (C) STRANDEDNESS: both
        (D) TOPOLOGY: linear (ii) MOLECULE TYPE: DNA (genomic)

(vi) ORIGINAL SOURCE:
        (A) ORGANISM: Enterobacter species (xi) SEQUENCE DESCRIPTION: SEQ ID NO: 5:

```
TGGCGTTAAC GGTCTGGCGA ACGCGGGCTA TATGTGGGAG TGCCCGGATC TCTTTCCGCT      60

GGCGGATACC TACCTGCTGA TCTGCTGCCC GCAGGGGCTG GCCCGTGAAG CGCAGCGCTT     120

TCTCAATACC TATCCTGCGG TGTGGATGGC AGGCCGCTTC GACGCCGAGC GCGGCACCTT     180

CAACCACGGC CCGCTGCACG AGCTGGACAG CGGGTTTGAG TTCTACGCGC CGCAGACCAT     240

GCTGGCCGAG GATGGCCGCC GTCTGCTGGT CGGCTGGATG GGCGTCCCGG ACGGGGAAGA     300

GATGCATCAA CCCACCCGCG CACAGGGATG GATCC                                335
```

(2) INFORMATION FOR SEQ ID NO: 6:

(i) SEQUENCE CHARACTERISTICS:
        (A) LENGTH: 357 base pairs
        (B) TYPE: nucleic acid
        (C) STRANDEDNESS: both
        (D) TOPOLOGY: linear (ii) MOLECULE TYPE: DNA (genomic)

(vi) ORIGINAL SOURCE:
        (A) ORGANISM: Enterobacter species (xi) SEQUENCE DESCRIPTION: SEQ ID NO: 6:

```
GGATCCTCAC CCACCCGGCG CTGACCAACG CCTGGGGCGT CGCCGCCGGC TTCCACACCA      60

TGAATTTCTT CGGCATCGAA GTGGCGATGA TCGGCTACCA GGGCACCGTC TTCCCGGTGC     120

TGCTGGCGGT GTGGTTTATG AGCATGGTCG AGAAACGGCT GCGCSSCGTT ATCCCTGACG     180

CGCTGGACCT GATCCTCACC CCGTTCCTGA CGGTGATTAT CTCCGGCTTT ATCGCCCTGC     240

TGCTGATCGG CCCGGCCGGT CGCGCGCTCG GCGACGGTAT TCGTTTATC CTCAGCACGC     300
```

```
TTATCAGCCA CGCCGGCTGG CTGGCGGGCC TGCTGTTCGG CGGCCTCTAC TCGGTGA        357
```

(2) INFORMATION FOR SEQ ID NO: 7:

(i) SEQUENCE CHARACTERISTICS:
        (A) LENGTH: 242 base pairs
        (B) TYPE: nucleic acid
        (C) STRANDEDNESS: both
        (D) TOPOLOGY: linear (ii) MOLECULE TYPE: DNA (genomic)

(vi) ORIGINAL SOURCE:
        (A) ORGANISM: Enterobacter species (xi) SEQUENCE DESCRIPTION: SEQ ID NO: 7:

```
CCGCCTGCTK TCCAACATTT TCGTACCGAT CATTCCCGCC ATCGTCSSCT CCGGCCTGCT         60
GATGGGCCTG CTGGGGATGG TGAAAACCTA CGGCTGGGTC GACCCGAGCA ACGCTATCTA        120
TATCATGCTG GATATGTGCA GCTCGGCAGC GTTTATCATT CTGCCGATCC TGATCGGCTT        180
TACCGCCGCC CGCGAATTTG GCGGTAACCC TTATCTGGGC GCGACCCTTG GCGGGATCCC        240
CG                                                                      242
```

(2) INFORMATION FOR SEQ ID NO: 8:

(i) SEQUENCE CHARACTERISTICS:
        (A) LENGTH: 255 base pairs
        (B) TYPE: nucleic acid
        (C) STRANDEDNESS: both
        (D) TOPOLOGY: linear (ii) MOLECULE TYPE: DNA (genomic)

(vi) ORIGINAL SOURCE:
        (A) ORGANISM: Enterobacter species (xi) SEQUENCE DESCRIPTION: SEQ ID NO: 8:

```
CTGCAGGACG CCGAAACCCG CGCCAGCACT GCCGAAAGCC GTGCCGCCTC GGCGGAGCAG         60
AAAGTTCAGC AGTTAACCCA GCAGCAGCAG CAAACCCAGG TCACCACCCA GCAGGTGGCC        120
AAGCGCACCA CTCAGCTGGA AGAAAAAGCC GAACGGCCTG GCGGCTTTGA GTTCCACGGC        180
TATGCCCGTT CCGGCGTGAT CATGAACGAC TCGGCCGCCA GCACCAAATC CGGCGCTTAT        240
ATGACCCCCG CCGGG                                                        255
```

(2) INFORMATION FOR SEQ ID NO: 9:

(i) SEQUENCE CHARACTERISTICS:
        (A) LENGTH: 246 base pairs
        (B) TYPE: nucleic acid
        (C) STRANDEDNESS: both
        (D) TOPOLOGY: linear (ii) MOLECULE TYPE: DNA (genomic)

(vi) ORIGINAL SOURCE:
        (A) ORGANISM: Enterobacter species (xi) SEQUENCE DESCRIPTION: SEQ ID NO: 9:

```
HTCTAGAGGA TCCGCAGGAC CTGCGTGACT GTCTCGACCG GGCGCTGGCC CTCGCCGACG         60
CCATAAAACT CTCGGAAGAG GAGCTGGCCT TTGTCAGCGG CAGCGACGAC ATCGTCAGCG        120
GCATCGCCCG GCTGAACGCC CGCTTCCAGC CGACGCTGCT GCTGGTGACC CAGGGCAAAG        180
CGGGGGTCCA GGCCGCCCTG CGCGGGCAGG TTAGCCACTT CCCCGCTCGC CCGGTGGTGG        240
CCGTTG                                                                  246
```

(2) INFORMATION FOR SEQ ID NO: 10:

(i) SEQUENCE CHARACTERISTICS:
        (A) LENGTH: 293 base pairs
        (B) TYPE: nucleic acid
        (C) STRANDEDNESS: both
        (D) TOPOLOGY: linear (ii) MOLECULE TYPE: DNA (genomic)

(vi) ORIGINAL SOURCE:
        (A) ORGANISM: Protaminobacter rubrum (xi) SEQUENCE DESCRIPTION: SEQ ID NO: 10:

```
GGATCCTGTC GATCGAAAAG ACTGCGCGCG AACACGGCTG GAACAGCTTT GTCGTCAACC    60

TGTTCGCCGA CGACAGCGCC GAACACACCA TAGACTTGCT GCTGGCGCAC CGGCCGGATG   120

GGGTGATTTT CACCACCATG GGGCTGCGAC AGGTCGCCGT GCCGCCCAAG TTACTGGATA   180

AAAAGCTGGT GCTGGCCAAC TGCGTCAGCA GGGAAATAGT GTTGCAGCTA CATTCGGATG   240

ACGAACAGGG CCAGTACGAC GCCATACGCG CGTTGATCGC CAAAGGCTAC CGY          293
```

(2) INFORMATION FOR SEQ ID NO: 11:

(i) SEQUENCE CHARACTERISTICS:
        (A) LENGTH: 919 base pairs
        (B) TYPE: nucleic acid
        (C) STRANDEDNESS: both
        (D) TOPOLOGY: linear (ii) MOLECULE TYPE: DNA (genomic)

(vi) ORIGINAL SOURCE:
        (A) ORGANISM: Protaminobacter rubrum (xi) SEQUENCE DESCRIPTION: SEQ ID NO: 11:

```
GCTGCGCGGC GAGACTCCCG CCCGCGCACC TCAATTTCAA TCCACGATAA AATCAAGTGA    60

GCCAATCCAA TGAACAATGC CTTAGCTCAA GCCGACCATG CGGTCGAAAC CCTGCGCGCA   120

CAGCGTCAAG ACGATTACTA CCCGCAATTT CATCTGGCGC CTGCCGCCGG CTGGATCAAC   180

GATCCCAATG GGTGGGTGTA CATTAACGGC GTTTATCATG CGTTCTATCA ACACCACCCC   240

TACGACGRAA ACTGGGGAMC GATGCACTGG GGCCACGCCA TCAGCCGGGA TCTGGCGCAC   300

TGGCAGCACC AGCCGATAGC CCTGTGCGCC CGGCGACGAC TACGACAAAG ACGGCTGTTT   360

CTCCGSTGCG CAGTGGACGA TAACGGCGTG CTGACGCTGA TCTACACCGG CCACGTCTGG   420

CTGGACAAAG TGGGCGATGA CGATCAGGTA CGCGAGGTAC AGTGCCTGGC CACCAGCGAG   480

GACGGCGTAC ATTTCGTCAA GCACGGGCCG GTGTTGGCGC CGCCGAAAGG CATTCAGCAT   540

TTCCGCGATC CCAAGGTCTG GCGCGAGAGT GACGGCTGGT GGATGGTGGT CGGCGCCAAA   600

CAAAACGGCC TCGGGCAGGC ACGGCTTTAT CGTTCAAAAG ATCTGCGTGA CTGGCAGTTT   660

GACCGCGTGC TGGACGGCGC GCAGACGCTG CATCAGGGCT ATATGTGGGA GTGCCCGGAT   720

TTCTTCCCTC TCGGCGAAAA ACAGGTGCTG CTGTTCTCGC CGCAGGGCT GGCGGCACAG   780

GGCTACCGCC ACCGTAACCG CTTCCAGAGC GGCTATTTGC TCGGTCACTG GCAGCCGGGC   840

GCTGATTTCA ACGTCACTCA ACCTTTCTGC GAACTGGACG CCGGGCATGA TTTCTATGCG   900

CCGCAAAMCT TTACMGSCG                                                919
```

(2) INFORMATION FOR SEQ ID NO: 12:

(i) SEQUENCE CHARACTERISTICS:
        (A) LENGTH: 327 base pairs (B) TYPE: nucleic acid
        (C) STRANDEDNESS: both
        (D) TOPOLOGY: linear (ii) MOLECULE TYPE: DNA (genomic)

(vi) ORIGINAL SOURCE:
        (A) ORGANISM: Protaminobacter rubrum (xi) SEQUENCE DESCRIPTION: SEQ ID NO: 12:

| | | | | | |
|---|---|---|---|---|---|
| AYTCGGTATC | AAACAAAGCC | TGCTGCTGGC | CAGCAGCGTG | GATGGGCGTT | TCGCATGTTC | 60 |
| GGCTCCGGCT | TCGCCAACGG | CGCGCTGATG | ATTTCCGCCA | TGAAACTGCT | GCATGCCGTG | 120 |
| GAGCTGCCGA | TTCTGCTGGT | AGCCATGTTC | AAATACATCA | CCACCCGCTT | TGACAGCCGC | 180 |
| CTGTCCTCCA | CGCTGTACCT | AGTGGGCTTC | CAGTTTATCA | GCCAGATCGT | CGCCGGCATT | 240 |
| CTGGCGCCCA | GCATGGCCAG | GTCATCGGCT | ACGACCGCAT | CGGTTTTGCC | GACACCTATT | 300 |
| TGCTGATGGT | GCGCCGTCGC | CRGTACC | | | | 327 |

(2) INFORMATION FOR SEQ ID NO: 13:

(i) SEQUENCE CHARACTERISTICS:
        (A) LENGTH: 1014 base pairs
        (B) TYPE: nucleic acid
        (C) STRANDEDNESS: both
        (D) TOPOLOGY: linear (ii) MOLECULE TYPE: DNA (genomic)

(vi) ORIGINAL SOURCE:
        (A) ORGANISM: Protaminobacter rubrum (xi) SEQUENCE DESCRIPTION: SEQ ID NO: 13:

| | | | | | |
|---|---|---|---|---|---|
| CGTGTTGAAA | CCCTGGTGGT | TCCCTGAGGA | GAATTTATGC | AAAACACCCA | TTTGCCGCCG | 60 |
| GGCCTGGCCC | CCTTTTCATT | GCTCGGCAAG | CGTGCACTGA | TCACCCGGGC | TACGCGAGGG | 120 |
| ATTGGTCAGG | CGCTGGCGAT | CGGGCTGGCG | CAGGCCGGTG | CGCAGGTGAT | CGTCGCCGGG | 180 |
| CGACAACGCG | CCGCGCTGCA | AGAGGTGGTA | CAACAGCTGA | ATAATTGGGG | AGAACACCCG | 240 |
| GAAATGCTGC | TGTTGGATGT | CCAGGATCCG | GCGTCGATTG | AAACCGCCTT | TGCCACGCTG | 300 |
| GCGGGCAAAC | CGCTGGATAT | CCTGATCAAC | AACGCCGGTA | TCGAACGCTT | GTGCCCGTCG | 360 |
| CTGGAGGTGG | ATGAAACGCT | GTGGGACAGC | GTCGTCGGCA | CCAACCTTAA | AGGCGCTTTC | 420 |
| TTCTGCGNGC | AGGCGGCGGC | GCGCCTGATG | GTCAAACAGG | GCAGCGGCAG | CATCATCAAC | 480 |
| CTGTGCTCAT | TGACCAGCGA | AGTCGGCGTG | CCGGGGGCTH | ACCTACGCG | CGTCAAAATC | 540 |
| CGGGCTGGCC | GGCATGACGC | GTGCGCTGGC | CAGCGAATGG | GCTACTACGG | GATCCGGGTC | 600 |
| AACGGCATCG | GGCCAGGCTA | TTTTCAGACC | GCGATGACCG | AGGTGTTTTA | CCAGGACAAC | 660 |
| GGTTGGCGCG | AGTCCATGCA | GGATAAAATT | CCGCTAGGCC | GTTTTGGCAA | GCTGAGCGAC | 720 |
| CTTACCGGTG | CGGCCATTTT | CCTCGCCGGC | CCGGCGGCGG | CCTACATCAC | CGGCCAGATC | 780 |
| CTGTATGTCG | ACGGCGGCTA | TCTGGCCAGC | ATCTGAATAA | ACGCAGGCGT | GGGCGATATC | 840 |
| CCGCCCACTC | TCCAGCGCCT | TGCATCCATC | CAGTGATGAC | GATCACAACG | CAAATATGTT | 900 |
| AACGTTAACT | TTTGTGATTA | ACATCGCAAT | CCCTGATGTT | GGTGGCTTTA | TTTGGCGAAA | 960 |
| GGTTAACGTT | AACAATAAGG | STGACATCAT | CCATCAGGGS | ATCTCACATG | AACN | 1014 |

(2) INFORMATION FOR SEQ ID NO: 14:

(i) SEQUENCE CHARACTERISTICS:
        (A) LENGTH: 335 base pairs
        (B) TYPE: nucleic acid
        (C) STRANDEDNESS: both -continued

```
        (D) TOPOLOGY: linear (ii) MOLECULE TYPE: DNA (genomic)

(vi) ORIGINAL SOURCE:
        (A) ORGANISM: Protaminobacter rubrum (xi) SEQUENCE DESCRIPTION: SEQ ID NO: 14:

GGATCCCACC GTCACCGCCG CTATCGCCTA TGCCGCCGGC AATATCCGCG CTTTTCACGA      60

AGCGCAGAAA CCGGAAGAAA TGTGGTTGAA AGAGATGCAG CCCGGCGCTT TGCCGGCGA     120

TCGCCACCTG CCGATCGATT CCGTAGCCTG CTATGTGCCG CGCGGCAAAG GTTCGTTCCC    180

CAGCGTGCTG CTGATGACGG CGATCCCGGC GCTGGTGGCC GGCGTACCCA GGCCGGTGGT    240

GATTACCCCS CCCGGCCCGG ATGGCAGAGT CGATGATGCC ACGCTGGTGG VGGCGCAGTT    300

GGTCGGCATC CGCGAAATTT ACAAGTGGCG GGGGG                               335
```